United States Patent
Zhao et al.

(10) Patent No.: US 9,312,503 B2
(45) Date of Patent: Apr. 12, 2016

(54) GREEN LIGHT IRIDIUM (III) COMPLEX AND A METHOD OF PREPARING THE SAME

(71) Applicant: Shenzhen China Star Optoelectronics Technology Co., Ltd., Shenzhen, Guangdong (CN)

(72) Inventors: Qiang Zhao, Guangdong (CN); Wei Huang, Guangdong (CN); Shujuan Liu, Guangdong (CN); Yifan Wang, Guangdong (CN); Qinghua Zou, Guangdong (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 0 days.

(21) Appl. No.: 14/398,121

(22) PCT Filed: May 28, 2014

(86) PCT No.: PCT/CN2014/078672
§ 371 (c)(1),
(2) Date: Oct. 30, 2014

(87) PCT Pub. No.: WO2015/172405
PCT Pub. Date: Nov. 19, 2015

(65) Prior Publication Data
US 2015/0357585 A1    Dec. 10, 2015

(30) Foreign Application Priority Data
May 13, 2014  (CN) .......................... 2014 1 0201799

(51) Int. Cl.
*C07F 15/00* (2006.01)
*H01L 51/50* (2006.01)
*H01L 51/00* (2006.01)
*C09K 11/06* (2006.01)

(52) U.S. Cl.
CPC ............ *H01L 51/0085* (2013.01); *C07F 15/00* (2013.01); *C07F 15/0033* (2013.01); *C09K 11/06* (2013.01); *H01L 51/5016* (2013.01); *C09K 2211/1007* (2013.01); *C09K 2211/1029* (2013.01); *C09K 2211/185* (2013.01)

(58) Field of Classification Search
USPC .............................................. 546/2; 313/504
See application file for complete search history.

(56) References Cited

U.S. PATENT DOCUMENTS 7,883,785 B2 * 2/2011 Stossel ................ C07F 15/0033
136/243
8,080,322 B2 * 12/2011 Tsuboyama ........... B82Y 20/00
313/502
2011/0260144 A1  10/2011 Lecloux

FOREIGN PATENT DOCUMENTS

| CN | 1678617 A | 10/2005 | |
|---|---|---|---|
| JP | 2013149880 A | 8/2013 | |
| WO | WO 2005/124889 A1 * | 12/2005 | ............ H01L 51/30 |
| WO | WO2005124889 A1 | 12/2005 | |

OTHER PUBLICATIONS

Tsuzuki, T. et al.: Color tunable organic light-emitting diodes using pentafluorophenyl-substituted Iridium complexes. Adv. Mater., vol. 15, pp. 1455-1458, 2003.*

* cited by examiner

*Primary Examiner* — Charanjit Aulakh
(74) *Attorney, Agent, or Firm* — Andrew C. Cheng

(57) ABSTRACT

The present invention provides a green light iridium (III) complex and a method of preparing the same, which has a formula as follows:

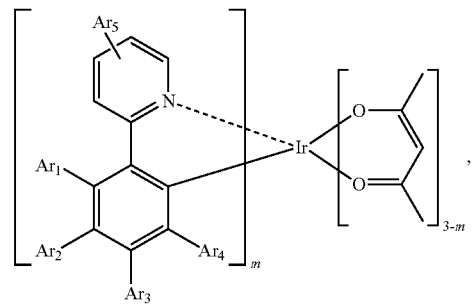

wherein m is 2 or 3; at least one of $Ar_1$, $Ar_2$, $Ar_3$, $Ar_4$, and $Ar_5$ is a group containing fluorophenyl unit, which has a formula as follows:

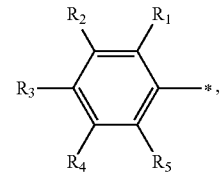

wherein $R_1$, $R_2$, $R_3$, $R_4$, $R_5$ are H, $CH_3$, or $FCF_3$, and at least one of $R_1$, $R_2$, $R_3$, $R_4$, $R_5$ is F or $CF_3$. The green light iridium (III) complex of the present invention has higher light emitting efficiency; the method of preparing the same has tender reaction conditions, simple synthesis steps and easy to handle. Due to the fluorophenyl unit capable of transporting electrons introduced therein, carrier current mobility and exciton transporting equilibrium are increased to contribute better exciton recombination so as to enhance performance of an organic electroluminescent device.

7 Claims, 6 Drawing Sheets

GREEN LIGHT IRIDIUM (III) COMPLEX AND A METHOD OF PREPARING THE SAME

FIELD OF THE INVENTION

The present invention relates to organic electroluminescent field, more particularly to a green light iridium (III) complex, a method of preparing the same and an organic electroluminescent device using the same.

BACKGROUND OF THE INVENTION

The organic electroluminescent device, also called the organic light-emitting diode (OLED), is a device that converts electrical energy into light energy by applying voltage thereon, and an ideal display for cell phones and color televisions. The OLED display has advantages of broad viewing angle, significant energy saving, high luminescence efficiency, etc. The unique advantages of the OLED closely relate to carrier transport, luminescence and electrode materials adopted therein and device structures in which the luminescence material is a core component of the OLED and can be divided into two types of fluorescent materials and phosphorescent materials.

The green light phosphor material of organic luminescence is one phosphorescent material on which has been earlier researched; undoubtedly, iridium complexes have been widely researched in the phosphorescent material.

It is based on heavy metal atoms of strong spin-orbit coupling mixed with singlet and triplet of complex in heavy metal complexes, so that an originally forbidden transition from triplet to ground state can be overcome, and then luminescent efficiency of the materials are greatly increased. In comparison of the iridium complexes and the other heavy metal complexes, the iridium complexes are convenient to handle and adjust color, and thus have been more widely researched.

As early as in 1999, team Forrest of Princeton University U.S.A. doped a phosphorescent iridium complex $Ir(ppy)_3$ in a host 4,4-N,N'-dicarbazole-biphenyl to obtain an OLED device having an external quantum efficiency of 8% and a power efficiency of 31 lm/w. Soon after, Ikai et al. further improved the host material and add a hole and exciton block layer to obtain a device doped with $Ir(ppy)_3$ having an external quantum efficiency increased to 19.2% by applying voltage of 3.52V thereon. Such low-voltage electroluminescence and luminescent efficiency of 72 lm/W allow the OLED be a uniform scattering light source for next generation power-saving display and illumination. Such excellent performance especially comes from effectively transferring all singlet and triplet of the host material to the object $Ir(ppy)_3$ so as to obtain a high external luminescent efficiency.

Then in 2000, team Forrest further doped $Ir(ppy)_3$ in several host materials having electron transporting performance to fabricate devices that had external quantum efficiency up to $(15.4\pm0.2)\%$ and maximum power efficiency of $(40\pm2)$ lm/W. In 2001, the team further reported a new green light phosphorescent material $Ir(ppy)_2acac$, they doped the phosphorescent material in TAZ to fabricate an organic electroluminescent device that had a maximum external up to $(19.0\pm1.0)\%$ and power efficiency up to $(60\pm5)$ lm/W; based on calculation, an internal quantum efficiency thereof is $(87\pm7)\%$, almost 100%, these fully shows prospect of phosphorescent material in application of electroluminescent field.

Such complex containing 2-phenylpyridine (ppy) as ligand has simple structures and excellent performance. Many research teams still try to discover synthesis of phosphorescent complex based on ppy and to research device performance.

Kim et al. reported a series of green light materials based on 2-phenylpyridine, they introduced methyl formed at different locations of phenyl and pyridine to synthesize 5 high efficiency green light materials in which have a maximum quantum efficiency of 52%; additionally, they further introduced some other large steric hindrance groups to synthesize some green light materials of novel structures, organic electroluminescent devices fabricated with the materials has a maximum external quantum efficiency of 25.6% and electric current efficiency up to 84.4 cd/A. Gao et al. synthesized a novel ligand BPPya based on change of 2-phenylpyridine and used the novel ligand to fabricate iridium complex $Ir(BPPya)_3$ having good luminescent efficiency and thermal stability. Since energy levels of object and subject material are close, an electroluminescent device based on the complex effectively reduces triplet-triplet quenching so as to have a maximum external quantum efficiency up to 14.6%, electric current efficiency of 52 cd/A and power efficiency of 33.5 lm/W. In 2013, He et al. synthesized a green light iridium complex; they used tfmppy as main ligand and tpip as auxiliary ligand, the synthesized complex has an emitting peak at 520 nm, a device fabricated by using high triplet level mCP as host material has an external quantum efficiency up to 20.8% and power efficiency up to 66.3 lm/W.

In recent years, with development of OLED technology, more and more high efficiency green light materials have been developed, and performance of recent green light OLED devices are getting better due to new technologies adopted to increase light extraction efficiency (such as light extraction technology, etc.)

In 2011, Helander et al., Toronto University reported the conventional ITO anode substituted with a chlorinated ITO anode, without hole injection and transport material, using $Ir(ppy)_2acac$ as light emitting material and adopting light extraction technology at the same time to fabricate green light devices that obtain an external quantum efficiency up to 54% and a power efficiency of 230 lm/W. Recently, Li et al., U.S.A reported a phosphorescent device structure using single-layer grapheme as anode and $Ir(ppy)_2acac$ still as object material, it allows holes from the single-layer grapheme directly inject into light emitting layer, the device has very excellent performance and an external quantum efficiency up to 60% by adopting the light extraction technology or 45% even at brightness of 10000 $cd/m^2$, and a color rending index (CRI) of the device is 85.

Although structures of the reported complexes based on 2-phenylpyridine are simple and have great advantages from the perspective of material synthesis, the complexes do not contain modified units of special functions; therefore, it is needed to modify device structures, due the materials do not have the special functions such as means of introducing a special carrier function layer or adopting complicated light extraction technologies, that allow the structures and art of the devices become cumbersome and complicated. On the other hand, for simplifying the organic electroluminescent device structure and fabrication arts, some special units can be introduced to the molecules such as dendrimers; however, it is undoubted to allow the material synthesis and preparation become cumbersome and complicated.

SUMMARY OF THE INVENTION

An object of the present invention is to provide a green light iridium (III) complex having higher luminescent efficiency, which contains special functional groups, that is fluorophenyl group capable of transporting electrons to contribute carrier transport equilibrium in recombination region so as to provide an organic electroluminescent device of better performance.

Another object of the present invention is to provide a method of preparing the green light iridium (III) complex which has tender reaction conditions, simple synthesis steps and easy to handle.

Another object of the present invention is to provide an organic electroluminescent device using the green light iridium (III) complex as a light emitting material and having excellent comprehensive performance.

For the aforesaid objects, the present invention provides a green light iridium (III) complex, which has a formula as follows:

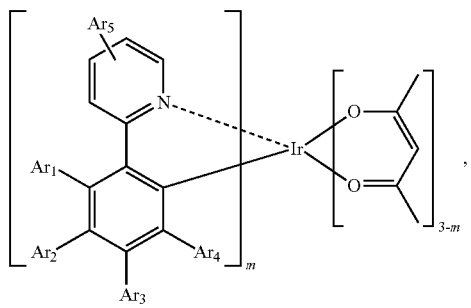

wherein m is 2 or 3, at least one of $Ar_1, Ar_2, Ar_3, Ar_4$ and $Ar_5$ is a group containing fluorophenyl unit, which has a formula as follows:

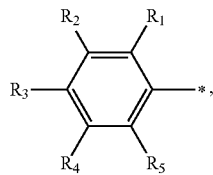

wherein R1, R2, R3, R4, R5 are H, CH3, or FCF3, and at least one of R1, R2, R3, R4, R5 is F or CF3.

In an embodiment, a formula of the group containing the fluorophenyl unit is as follows:

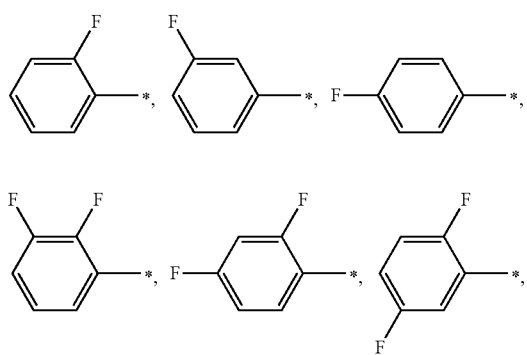

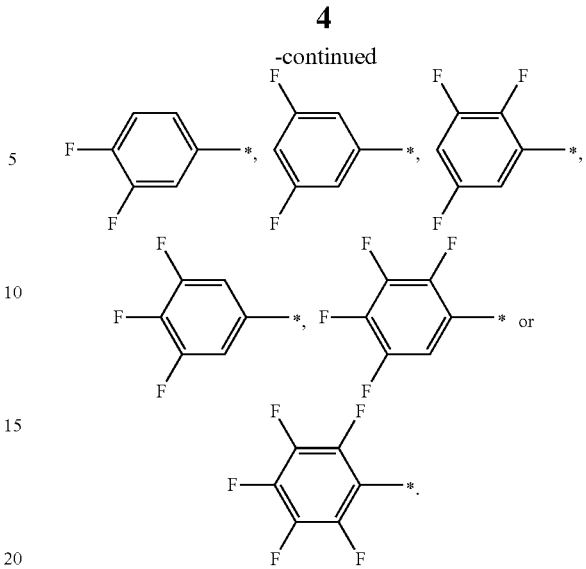

In an embodiment, a formula of the group containing the fluorophenyl unit is as follows:

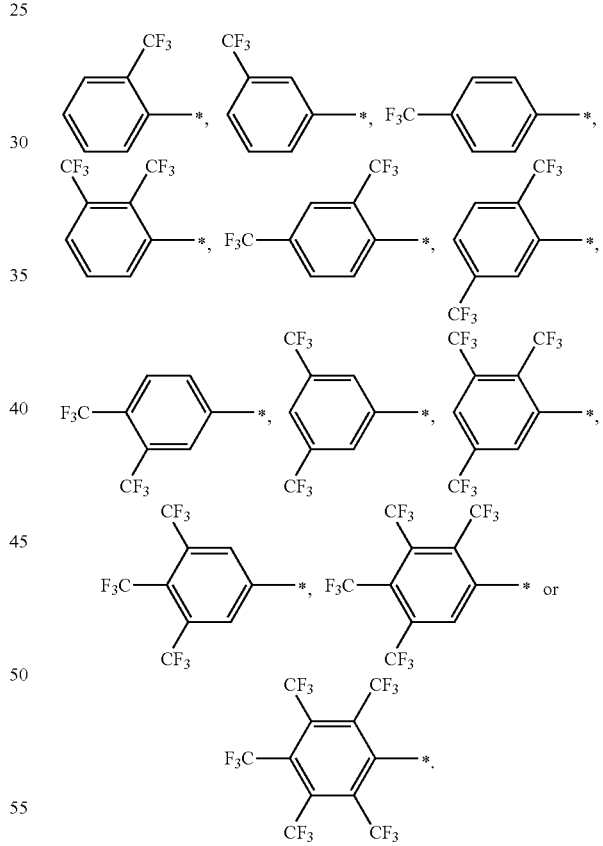

In an embodiment, the green light iridium (III) complex is Ir(dfbppy)$_2$acac.

The present invention further provides a method of preparing the green light iridium (III) complex using m-dibromobenzene as raw material through a synthesis of five steps, including:

step 1, synthesizing an intermediate 1(3-(4,4,5,5-tetramethyl-1,3,2-dioxaborolan-2-yl) bromobenzene);

step 2, synthesizing an intermediate 2 (2-(3-bromo-phenyl)-pyridine);

step 3, synthesizing an intermediate 3 (2-(3-(2,4-difluorophenyl)-phenyl)-pyridine);

step 4, synthesizing an intermediate 4 ([Ir(dfbppy)$_2$]$_2$Cl$_2$); and step 5, synthesizing a target product (Ir(dfbppy)$_2$acac).

In each step, specifically, step 1, including: adding m-dibromobenzene of 4.24 mmol, bis(pinacolato)diboron of 4.24 mmol, 1,1'-bis(diphenylphosphino)ferrocene-palladium(II) dichloride dichloromethane complex of 0.212 mmol, potassium acetate of 600 mg and 1,4-dioxane of 20 mL into a dual-port reaction flask through three cycles of evacuation-nitrogen purge-evacuation; protecting the reaction system with nitrogen; refluxing under 85° C. for 10 hours, then stop the reaction; removing solvent by using a rotary evaporator; separating the intermediate 1 (3-(4,4,5,5-tetramethyl-1,3,2-dioxaborolan-2-yl) bromobenzene) by using a column chromatography.

Step 2, including: adding 2-bromo-pyridine of 2.26 mmol, the intermediate 1 of 2.49 mmol and tetrakis(triphenylphosphine)palladium of 0.04 mmol into a dual-port flask through three cycles of evacuation-nitrogen purge-evacuation; protecting the reaction system with nitrogen; injecting a deoxidized and mixed solvent having a mixing ration of 3:1:1 (toluene:ethanol:sodium carbonate solution, V/V/V) into the reaction flask;reacting the reaction system under 80° C. for 6 hours; extracting with dichloromethane and water by three times, then combining organic phase; removing the solvent by using the rotary evaporator; separating the intermediate 2 (2-(3-bromo-phenyl)-pyridine) by using the column chromatography.

Step 3, including: adding the intermediate 2 of 1.28 mmol, 2,4-difluorobenzeneboronic acid of 1.41 mmol and tetrakis (triphenylphosphine)palladium of 0.03 mmol into a dual-port flask through three cycles of evacuation-nitrogen purge-evacuation; protecting the reaction system with nitrogen; injecting a deoxidized and mixed solvent having a mixing ration of 3:1:1 (toluene:ethanol:sodium carbonate solution, V/V/V) into the reaction flask; reacting the reaction system under 80° C. for 6 hours; extracting with dichloromethane and water by three times, then combining organic phase; removing the solvent by using the rotary evaporator; separating the intermediate 3 (2-(3-(2,4-difluorophenyl)-phenyl)-pyridine) by using the column chromatography.

Step 4, including: weighting and adding IrCl$_3$.3H$_2$O (0.288 mmol) and the intermediate 3 (0.72 mmol) into two-neck bottle through three cycles of evacuation-nitrogen purge-evacustion; protecting the reaction system with nitrogen; injecting a mixture of 2-eyhoxyethanol and water (3:1, v/v), then heating the reaction mixture to 110° C.; stirring and reacting for 24 hours; after the reaction stopped, cooling the reaction mixture to room temperature; filtrating to obtain precipitation; respectively washing the precipitation with water to obtain the intermediate 4 ([Ir(dfbppy)$_2$]$_2$Cl$_2$).

Step 5, including: weighting and adding the obtained iridium dichloro bridge compound of 0.02 mmol, acetylacetone of 0.05 mmol and potassium carbonate powder of 20 equivalents into a dual-port flask through three cycles of evacuation-nitrogen purge-evacuation; protecting the reaction system with nitrogen; injecting 2-eyhoxyethanol of 5mL; reacting under dry nitrogen circumstance for 6 hours; after the reaction stopped, removing the solvent by using the rotary evaporator; separating the target product Ir(dfbppy)$_2$acac by using the column chromatography.

The present invention further provides an organic electroluminescent device using the aforesaid green light iridium (III) complex as a light emitting material.

Advantages of the present invention: the green light iridium (III) complex according to the present invention, due to the effect of the heavy metal atoms in the heavy metal complex, the iridium (III) complex can sufficiently use energy of triplet excitons to increase luminescent efficiency of the material. The method of preparing the same has tender reaction conditions, simple synthesis steps and easy to handle. Due to the fluorophenyl unit capable of transporting electrons introduced therein, carrier current mobility and exciton transporting equilibrium are increased and improved to contribute better exciton recombination so as to enhance performance of an organic electroluminescent device.

The above objects and advantages of the present invention will become more readily apparent after reviewing the following detailed description and accompanying drawings. It is to be noted that the following descriptions of preferred embodiments of this invention are presented herein for purpose of illustration and description only. It is not intended to be exhaustive or to be limited to the precise form disclosed.

BRIEF DESCRIPTION OF THE DRAWINGS

The above objects and advantages of the present invention will become more readily apparent to those ordinarily skilled in the art after reviewing the following detailed description and accompanying drawings, in which.

DETAILED DESCRIPTION OF PREFERRED EMBODIMENTS

Figure 1:
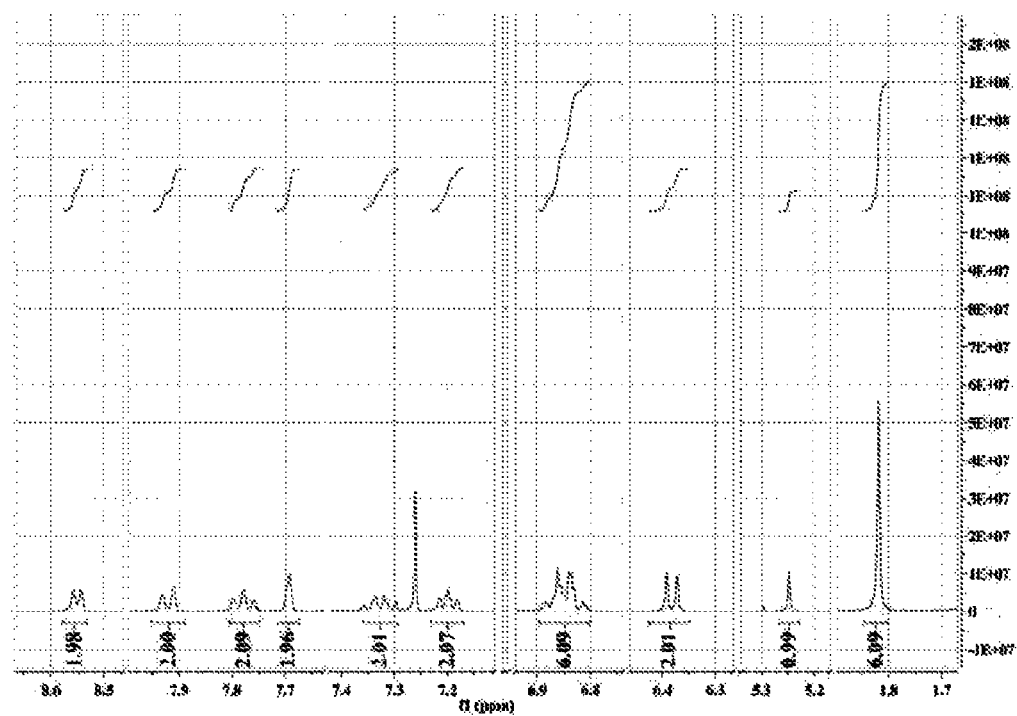
FIG. 1 is an NMR spectra of the complex Ir(dfbppy)$_2$acac.

The present invention will now be described more specifically with reference to the following embodiments.

The present invention provides a green light iridium (III) complex, which has a formula as follows:

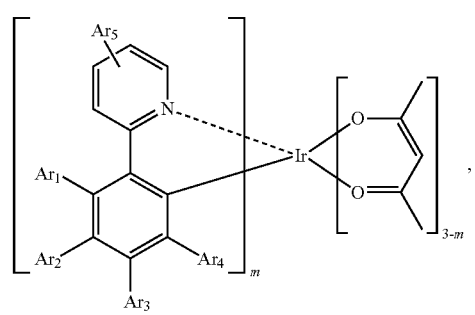

wherein m is 2 or 3; at least one of $Ar_1$, $Ar_2$, $Ar_3$, $Ar_4$ and $Ar_5$ is a group containing fluorophenyl unit, which has a formula as follows:

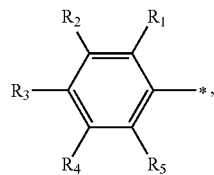

wherein R1, R2, R3, R4, R5 are H, CH3, or FCF3, and at least one of R1, R2, R3, R4, R5 is F or CF3.

In case of group F, a formula of the group containing fluorophenyl unit is as follows:

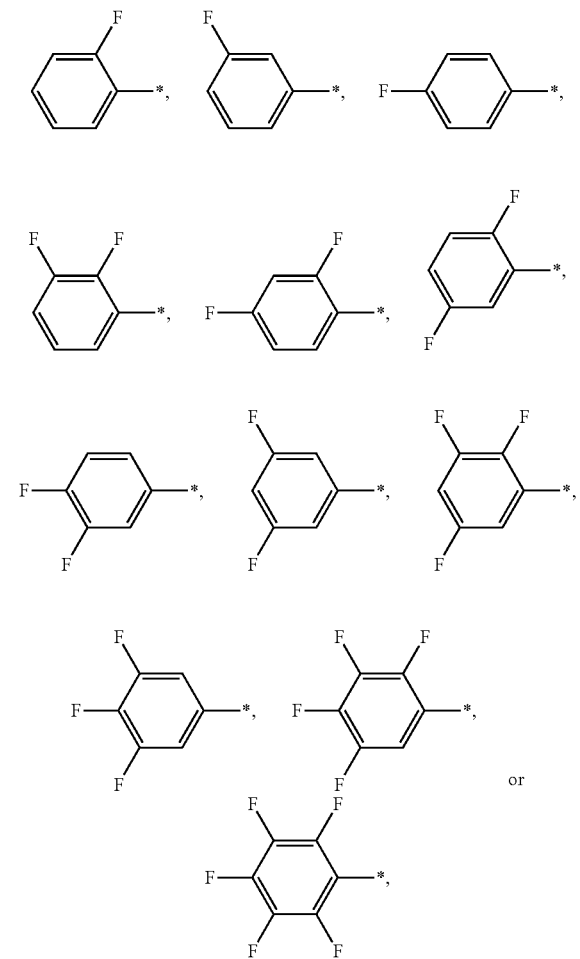

In case of group $CF_3$, a formula of the group containing fluorophenyl unit is as follows:

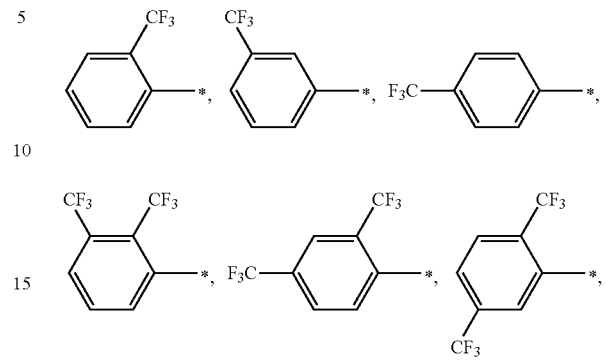

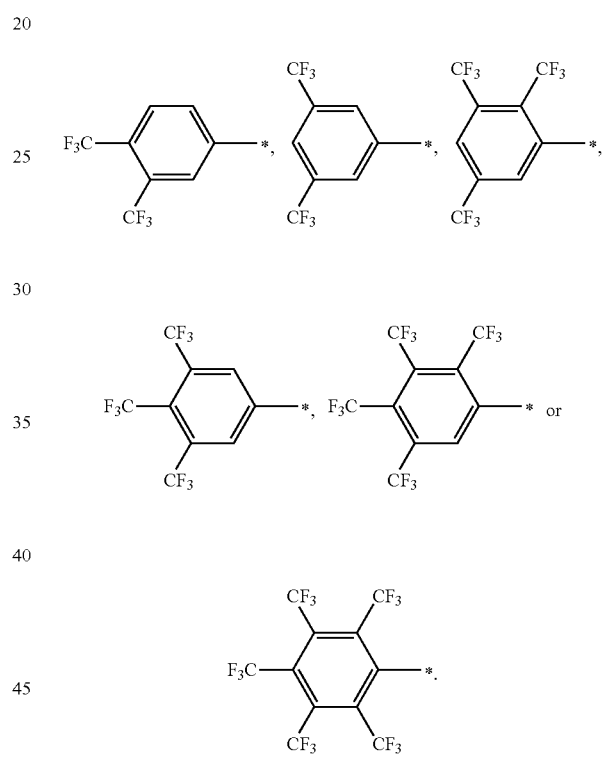

In a preferred embodiment, The green light iridium (III) complex is $Ir(dfbppy)_2acac$.

According to an embodiment of the present invention, A method of preparing the green light iridium (III) complex $Ir(dfbppy)_2acac$, using m-dibromobenzene as a raw material through a synthesis of five steps, includes following reaction formula:

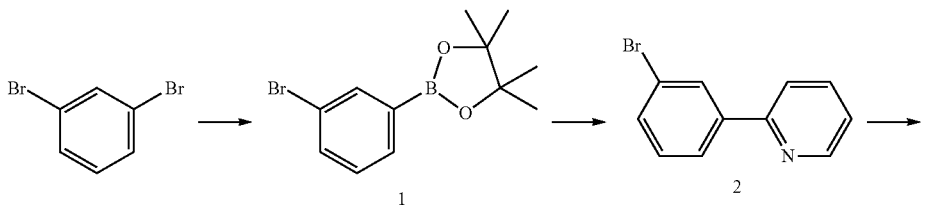

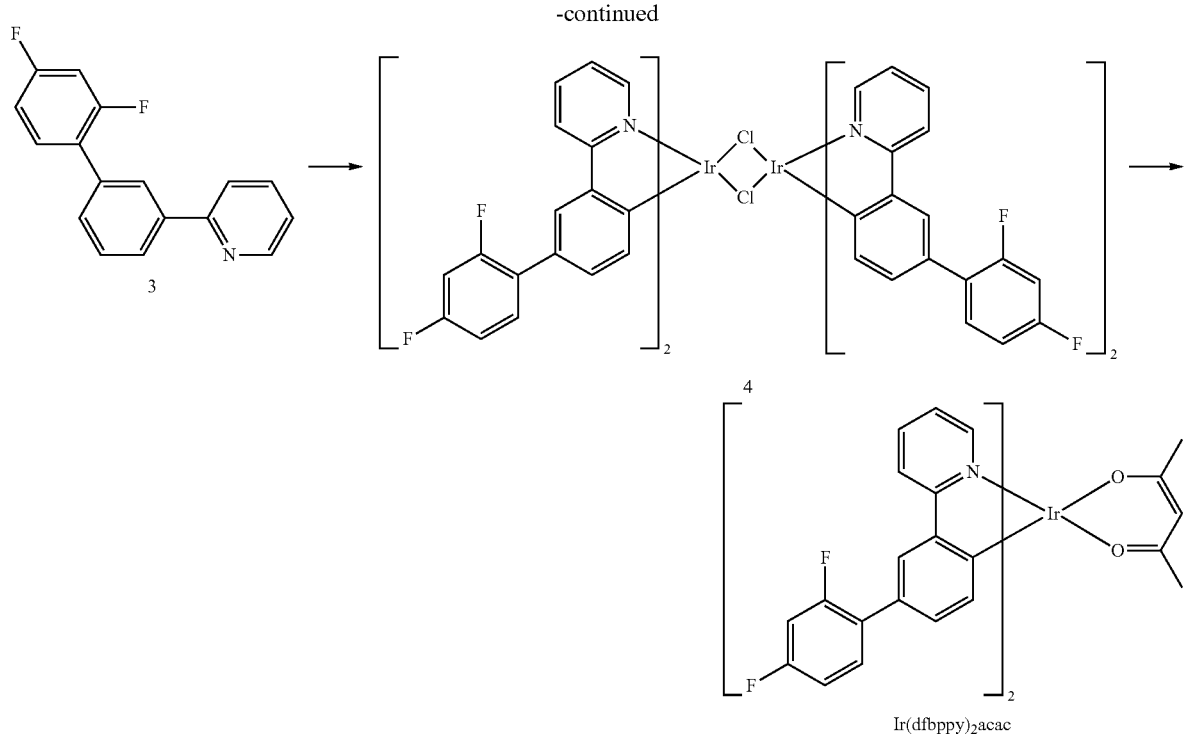

Ir(dfbppy)₂acac

Step 1, synthesis of an intermediate 1 (3-(4,4,5,5-tetramethyl-1,3,2-dioxaborolan-2-yl) bromobenzene) includes:
adding m-dibromobenzene of 4.24 mmol, bis(pinacolato) diboron of 4.24 mmol, 1,1'-bis(diphenylphosphino)ferrocene-palladium(II)dichloride dichloromethane complex of 0.212 mmol, potassium acetate of 600 mg and 1,4-dioxane of 20 mL into a dual-port reaction flask through three cycles of evacuation-nitrogen purge-evacuation on a double row tube; finally, protecting the reaction system with nitrogen; refluxing under 85° C. for 10 hours, then stop the reaction; removing solvent by using a rotary evaporator; separating white solid by using a column chromatography.

The obtained intermediate 1 (3-(4,4,5,5-tetramethyl-1,3,2-dioxaborolan-2-yl)bromobenzene is examined through $^1$H NMR, and has a correct structure revealed in the $^1$H NMR spectra data as follows:

$^1$H NMR (400 MHz, CDCl$_3$) δ(ppm)=7.93 (s, 1H), 7.71 (d, J=7.6 Hz, 1H), 7.58 (ddd, J=8.0, 2.0, 1.2 Hz, 1H), 7.23 (t, J=7.6 Hz, 1H), 1.34 (s, 12H).

Step 2, synthesis of an intermediate 2 (2-(3-bromo-phenyl)-pyridine) includes : adding 2-bromo-pyridine of 2.26 mmol, the intermediate 1 of 2.49mmol and tetrakis(triphenylphosphine)palladium of 0.04 mmol into a dual-port flask through three cycles of evacuation-nitrogen purge-evacuation on the double row tube; finally, protecting the reaction system with nitrogen, then injecting a deoxidized and mixed solvent having a mixing ration of 3:1:1 (toluene:ethanol:sodium carbonate solution, V/V/V) with a syringe into the reaction flask; reacting the reaction system under 80° C. for 6 hours; after the reaction stopped, extracting with dichloromethane and water by three times, then combining organic phase; removing the solvent by using a rotary evaporator; separating colorless liquid by using the column chromatography.

The obtained intermediate 2 (2-(3-bromo-phenyl)-pyridine) is examined through $^1$H NMR, and has a correct structure revealed in the $^1$H NMR spectra data as follows:

$^1$H NMR (400 MHz, CDCl$_3$) δ(ppm)=8.70 (d, J=4.8 Hz, 1H), 8.18 (t, J=1.2 Hz, 1H), 7.91 (d, J=7.6 Hz, 1H), 7.77 (dt, J=8.0, 1.5 Hz, 1H), 7.71 (d, J=8.0 Hz, 1H), 7.54 (dd, J=8.0, 0.8 Hz, 1H), 7.34 (t, J=8.0 Hz, 1H), 7.27 (t, J=6.2 Hz, 1H).

Step 3, synthesis of the intermediate 3 (2-(3-(2,4-difluorophenyl)-phenyl)-pyridine) includes:
adding the intermediate 2 of 1.28 mmol, 2,4-difluorobenzeneboronic acid of 1.41 mmol and tetrakis(triphenylphosphine)palladium of 0.03 mmol into a dual-port flask through three cycles of evacuation-nitrogen purge-evacuation; finally, protecting the reaction system with nitrogen, then injecting a deoxidized and mixed solvent having a mixing ration of 3:1:1 (toluene:ethanol:sodium carbonate solution, V/V/V) with a syringe; reacting the reaction system under 80° C. for 6 hours; after the reaction stopped, extracting with dichloromethane and water by three times, then combining organic phase; removing the solvent by using the rotary evaporator; separating white solid by using the column chromatography.

The obtained intermediate 3 (2-(3-(2,4-difluorophenyl)-phenyl)-pyridine) is examined through $^1$H NMR, and has a correct structure revealed in the $^1$H NMR spectra data as follows:

$^1$H NMR (400 MHz, CDCl$_3$) δ(ppm)=8.71 (dt, J=8.4, 1.6 Hz, 1H), 8.14 (s, 1H), 8.04-7.94 (m, 1H), 7.77 (dd, J=3.6, 1.2 Hz, 2H), 7.55 (d, J=5.2 Hz, 2H), 7.49 (dt, J=6.4, 8.8 Hz, 1H), 7.31-7.20 (m, 1H), 7.02-6.88 (m, 2H).

Step 4, synthesis the intermediate 4 ([Ir(dfbppy)$_2$]$_2$Cl$_2$):
weighting and adding IrCl$_3$.3H$_2$O (0.288 mmol) and the intermediate 3 (0.72 mmol) into a two-neck bottle through three cycles of evacuation-nitrogen purge-evacuation; finally, protecting the reaction system with nitrogen; injecting a mixture of 2-eyhoxyethanol and water (3:1,v/v) with a syringe, then heating the reaction mixture to 110° C.; stirring and reacting for 24 hours; after the reaction stopped, cooling the reaction mixture to room temperature; filtrating to obtain precipitation; respectively washing the precipitation with water and ethanol to obtain pale yellow solid iridium dichloro bridge compound.

Step 5, synthesis a target product (Ir(dfbppy)$_2$acac) includes:

weighting the obtained iridium dichloro bridge compound of 0.02 mmol, acetylacetone of 0.05 mmol and potassium carbonate powder of 20 equivalents into a dual-port flask through three cycles of evacuation-nitrogen purge-evacuation on the double row tube; protecting the reaction system with nitrogen; injecting 2-eyhoxyethanol of 5 mL with a syringe; reacting under dry nitrogen circumstance for 6 hours; after the reaction stopped, removing the solvent by using the rotary evaporator; separating pale yellow solid Ir(dfbppy)$_2$acac by using the column chromatography.

Figure 2:
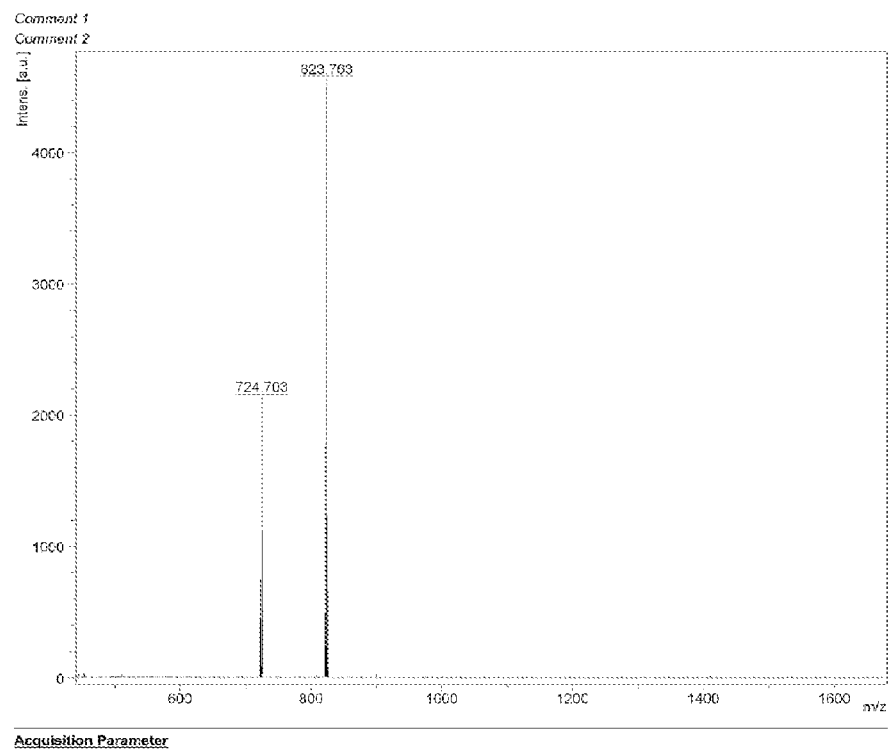
FIG. 2 is a Mass spectra of the complex Ir(dfbppy)$_2$acac.

The obtained target product Ir(dfbppy)$_2$acac is examined through $^1$H NMR and Mass, the NMR spectra and Mass spectra thereof respectively as shown in FIG. 1 and FIG. 2, and the obtained target product Ir(dfbppy)$_2$acac has a correct structure revealed in the spectra data as follows:

$^1$H NMR (400 MHz, CDCl$_3$) δ(ppm)=8.55 (d, J=5.2 Hz, 2H), 7.92 (d, J=8.0 Hz, 2H), 7.77 (dt, J=1.6, 6.8 Hz, 2H), 7.69 (t, J=1.6 Hz, 2H), 7.33 (dt, J=6.8, 8.8 Hz, 2H), 7.20 (ddd, J=0.8, 5.6, 6.8 Hz, 2H), 6.89-6.81 (m, 6H), 6.38 (d, J=7.6 Hz, 2H), 5.25 (s, 1H), 1.82 (s, 6H).

As shown in FIG. 2, the experimental molecular weight of the target product is 823.76, the theoretical molecular weight of the complex Ir(dfbppy)$_2$acac is 823.9, the two molecular weights are very close that represents the target product is the Ir(dfbppy)$_2$acac.

Figure 3:
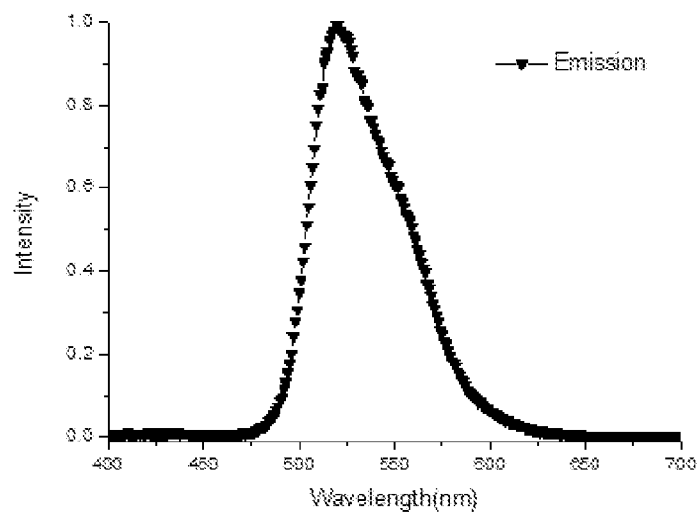
FIG. 3 is a photoluminescence spectra of the complex Ir(dfbppy)$_2$acac.

Please refer to FIG. 3, as shown in the photoluminescence spectra of the complex Ir(dfbppy)$_2$acac, a emitting peak of the complex Ir(dfbppy)$_2$acac is at 520 nm.

Figure 4:
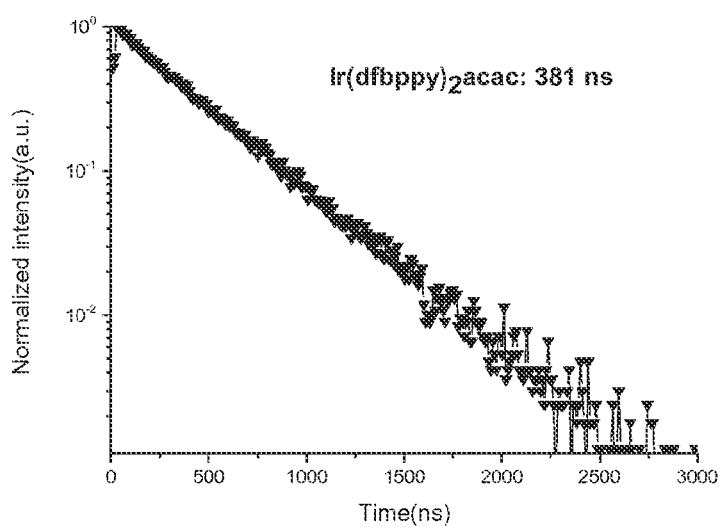
FIG. 4 is a phosphorescence lifetime map of the complex Ir(dfbppy)$_2$acac.

Please refer to FIG. 4, as shown in the phosphorescence lifetime map of the comple Ir(dfbppy)$_2$acac, phosphorescent emission intensity of the complex Ir(dfbppy)$_2$acac shows a single exponential decay, and the complex has phosphorescent lifetime of 381 ns.

Figure 5:
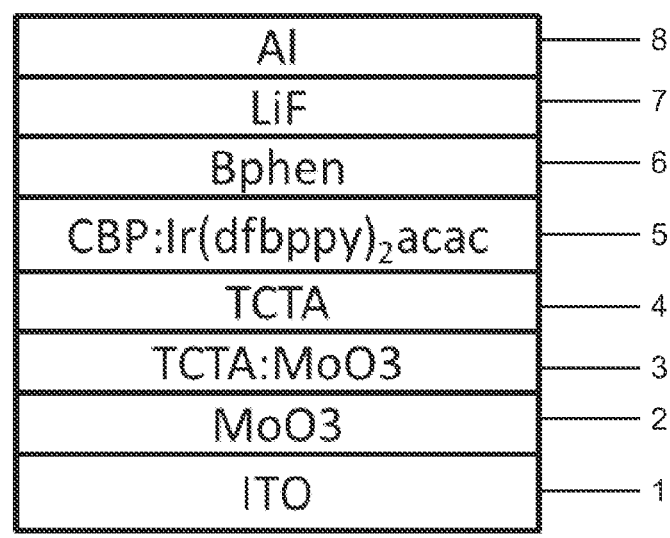
FIG. 5 is a structural view illustrating an organic electroluminescent device using the complex Ir(dfbppy)$_2$acac as the light emitting material.

The present invention further provides an organic electroluminescent device using the aforesaid green light iridium (III) complex as a light emitting material. Please refer to FIG. 5, the device includes: anode 1, hole injection layer 2, hole injection layer 3, hole transport layer 4, light emitting layer 5, electron transport layer 6, electron injection layer 7 and cathode 8.

The anode 1 is indium tin oxide (ITO); the hole injection layer 2 is molybdenum oxide (MoO$_3$); the hole injection 3 is a mixture of 4,4',4'-tris(carbazol-9-yl)-triphenylamine (TCTA) and MoO$_3$; the hole transport layer 4 is TCTA; the light emitting layer 5 is a mixture of 4,4'-bis(9-carbazolyl)-1,1'-biphenyl (CBP) and the Ir(dfbppy)$_2$acac; the electron transport layer 6 is 1,10-phenanthroline, 4,7-diphenyl (Bphen); the electron injection layer 7 is lithium fluoride (LiF); and the cathode 8 is aluminum (Al).

Figure 6:
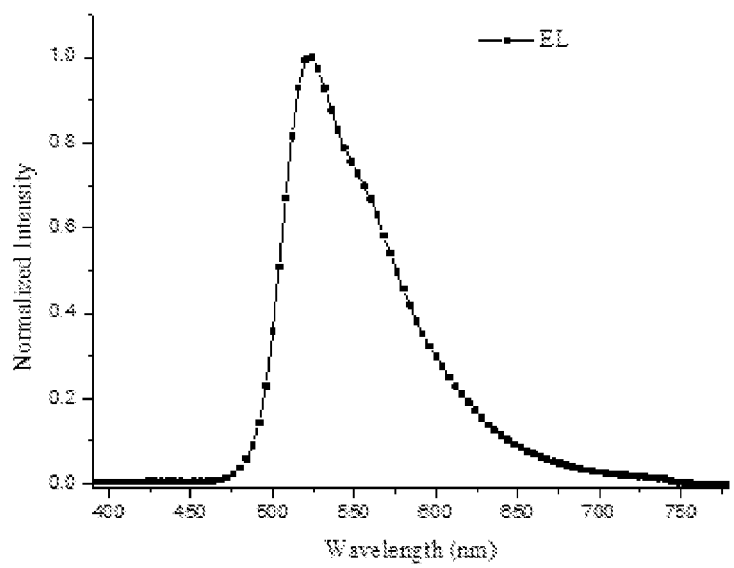
FIG. 6 is a electroluminescence spectra of the organic electroluminescent device using the complex Ir(dfbppy)$_2$acac as the light emitting material.

FIG. 6 is an electroluminescence spectra of the organic electroluminescent device using the complex Ir(dfbppy)2acac as the light emitting material. As shown in FIG. 6, an emitting peak of the organic electroluminescent device is at 520 nm.

Figure 7:
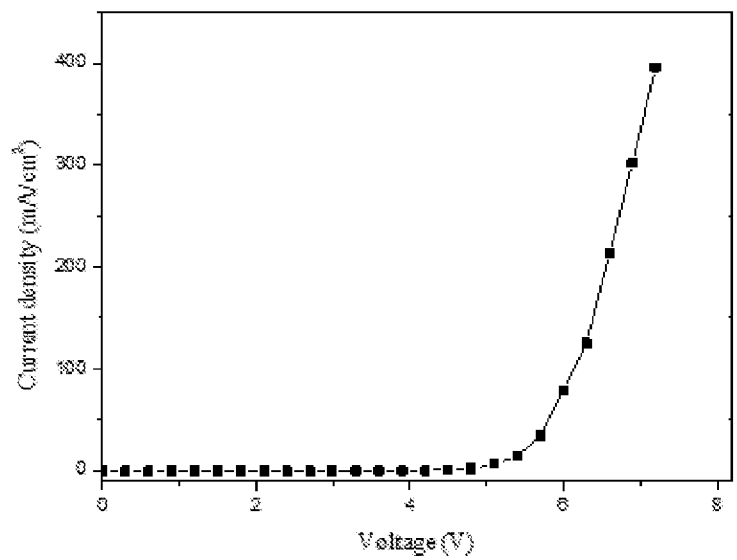
FIG. 7 is a current density & voltage map of the organic electroluminescent device using the complex Ir(dfbppy)$_2$acac as the light emitting material.

FIG. 7 is a current density & voltage map of the organic electroluminescent device using the complex Ir(dfbppy)$_2$acac as the light emitting material. As shown in FIG. 7, a starting voltage of the organic electroluminescent device is about 3.3V.

Figure 8:
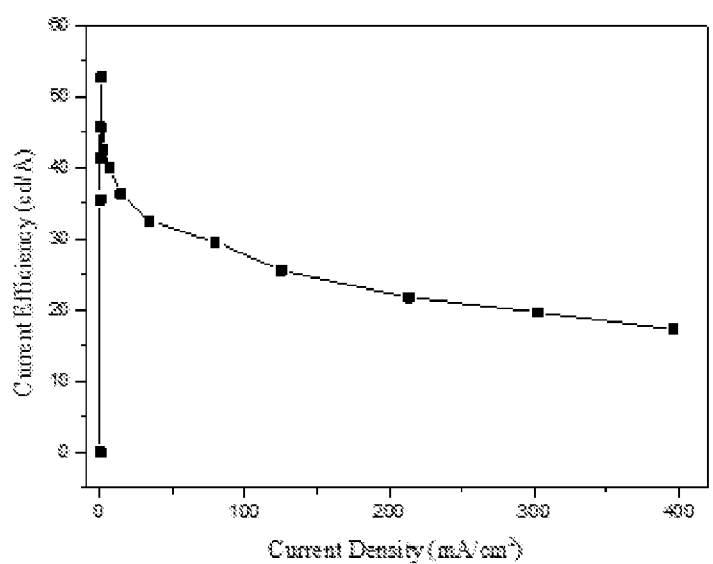
FIG. 8 is a current efficiency & current density map of the organic electroluminescent device using the complex Ir(dfbppy)$_2$acac as the light emitting material.

FIG. 8 is a current efficiency & current density map of the organic electroluminescent device using the complex Ir(dfbppy)$_2$acac as the light emitting material. As shown in FIG. 8, a maximum current efficiency of the organic electroluminescent device is 52cd/A.

Figure 9:
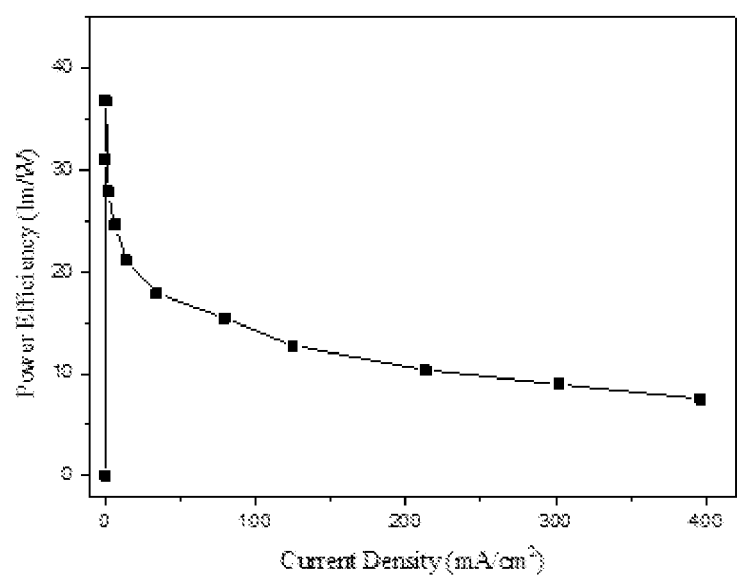
FIG. 9 is a power efficiency & current density map of the organic electroluminescent device using the complex Ir(dfbppy)$_2$acac as the light emitting material.

FIG. 9 is a power efficiency & current density map of the organic electroluminescent device using the complex Ir(dfbppy)$_2$acac as the light emitting material. As shown in FIG. 9, a maximum power efficiency of the organic electroluminescent device is 37 lm/W.

In summary, the green light iridium (III) complex according to the present invention introduce the fluorophenyl group capable of transporting electrons to synthesize a novel green light iridium (III) complex based on a modification of 2-phenylpyridine. The method of preparing the same has tender reaction conditions, simple synthesis steps and easy to handle. Due to the effect of the heavy metal atoms in the heavy metal complex, the iridium (III) complex can sufficiently use energy of triplet excitons to increase luminescent efficiency of the material. Due to the fluorophenyl unit capable of transporting electrons introduced therein, carrier current mobility and exciton transporting equilibrium are increased and improved to contribute better exciton recombination so as to enhance performance of an organic electroluminescent device.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An green light iridium (III) complex, wherein the green light iridium (III) complex is Ir(dfbppy)$_2$acac having a formula as

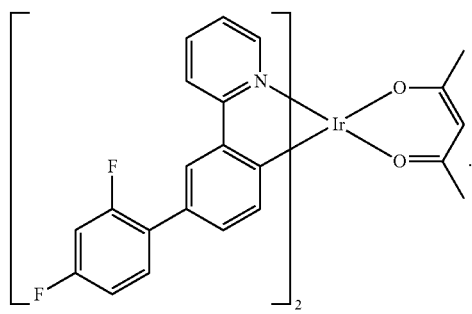

2. A method of preparing the green light iridium (III) complex according to claim 1, using m-dibromobenzene as a raw material through a synthesis of five steps, comprising:

step 1, synthesizing an intermediate 1 (3-(4,4,5,5-tetramethyl-1,3,2-dioxaborolan-2-yl) bromobenzene);

step 2, synthesizing an intermediate 2 (2-(3-bromo-phenyl)-pyridine);

step 3, synthesizing an intermediate 3 (2-(3-(2,4-difluorophenyl)-phenyl)-pyridine);

step 4, synthesizing an intermediate 4 ([Ir(dfbppy)$_2$]$_2$Cl$_2$); and step 5, synthesizing a target product (Ir(dfbppy)$_2$acac).

3. The method of preparing the green light iridium (III) complex according to claim 2, wherein the step 1 comprises:

adding m-dibromobenzene of 4.24 mmol, bis(pinacolato)diboron of 4.24 mmol, 1,1'-bis(diphenylphosphino)ferrocene-palladium(II)dichloridedichloromethane complex of 0.212 mmol, potassium acetate of 600 mg and 1,4-dioxane of 20 mL into a dual-port reaction flask through three cycles of evacuation-nitrogen purge-evacuation; protecting the reaction system with nitrogen, refluxing under 85° C. for 10 hours, then stop the reaction; removing solvent by using a rotary evaporator, separating the intermediate 1 (3-(4,4,5,5-tetramethyl-1,3,2-dioxaborolan-2-yl) bromobenzene) by using a column chromatography.

4. The method of preparing the green light iridium (III) complex according to claim 3, wherein the step 2 comprises: adding 2-bromo-pyridine of 2.26 mmol, the intermediate 1 of 2.49 mmol and tetrakis(triphenylphosphine)palladium of 0.04 mmol into a dual-port flask through three cycles of evacuation-nitrogen purge-evacuation; protecting the reaction system with nitrogen; injecting a deoxidized and mixed solvent having a mixing ration of 3:1:1 (toluene:ethanol:sodium carbonate solution, V/V/V) into the reaction flask; reacting the reaction system under 80° C. for 6 hours; extracting with dichloromethane and water by three times, then combining organic phase; removing the solvent by using the rotary evaporator; separating the intermediate 2 (2-(3-bromo-phenyl)-pyridine) by using the column chromatography.

5. The method of preparing the green light iridium (III) complex according to claim 4, wherein the step 3 comprises: adding 1.28 mmol the intermediate 2 of 1.28 mmol, 2,4-difluorobenzeneboronic acid of 1.41 mmol and tetrakis(triphenylphosphine)palladium of 0.03 mmol into a dual-port flask through three cycles of evacuation-nitrogen purge-evacuation; protecting the reaction system with nitrogen; injecting a deoxidized and mixed solvent having a mixing ration of 3:1:1 (toluene:ethanol:sodium carbonate solution, V/V/V) into the reaction flask; reacting the reaction system under 80° C. for 6 hours; extracting with dichloromethane and water by three times, then combining organic phase; removing the solvent by using the rotary evaporator; separating the intermediate 3 (2-(3-(2,4-difluorophenyl)-phenyl)-pyridine) by using the column chromatography.

6. The method of preparing the green light iridium (III) complex according to claim 5, wherein the step 4 comprises: weighting and adding $IrCl_3 \cdot 3H_2O$ (0.288 mmol) and the intermediate 3 (0.72 mmol) into a two-neck bottle through three cycles of evacuation-nitrogen purge-evacuation; protecting the reaction system with nitrogen; injecting a mixture of 2eyhoxyethanol and water (3:1, v/v), then heating the reaction mixture to 110° C.; stirring and reacting for 24 hours; after the reaction stopped, cooling the reaction mixture to room temperature; filtrating to obtain precipitation; respectively washing the precipitation with water and ethanol to obtain the intermediate 4 ($[Ir(dfbppy)_2]_2Cl_2$;

the step 5 comprises: weighting and adding the obtained iridium dichloro bridge compound of 0.02 mmol, acetylacetone of 0.05 mmol and potassium carbonate powder of 20 equivalents into a dual-port flask through three cycles of evacuation-nitrogen purge-evacuation; protecting the reaction system with nitrogen; injecting 2-eyhoxyethanol of 2 mL; reacting under dry nitrogen circumstance for 6 hours; after the reaction stopped, removing the solvent by using the rotary evaporator; separating the target product $Ir(dfbppy)_2acac$ by using the column chromatography.

7. An organic electroluminescent device using the green light iridium (III) complex according to claim 1 as a light emitting material.

* * * * *